United States Patent [19]

Hrebeniuk

[11] Patent Number: Plant 6,990

[45] Date of Patent: Aug. 15, 1989

[54] DISTINCT VARIETY OF POINSETTIA NAMED WONDER STAR II

[76] Inventor: Alexander Hrebeniuk, R.D. #1, Box 118, Sugar Run, Pa. 18846

[21] Appl. No.: 178,331

[22] Filed: Apr. 6, 1988

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Webb, Burden, Ziesenheim & Webb

[57] ABSTRACT

A poinsettia plant named Wonder Star II particularly characterized by the combined characteristics of dark red and fade resistant bracts, dark green foliage, double compact form, long lasting keeping qualities and adaptability for basket presentation.

1 Drawing Sheet

BACKGROUND OF THE NEW PLANT

The present invention comprises a new and distinct cultivar of *Euphorbia pulcherrima* known by the varietal name Wonder Star II (H320). The new cultivar was developed in a breeding program and is a seedling resulting from the cross of the seed parent H-365 (U.S. Plant Pat. No. 6,491) and the pollen parent Wonder Star (U.S. Plant Pat. No. 3,917).

The new cultivar was discovered in November of 1986 in Sugar Run, Pa.; was first asexually reproduced by cuttings in May of 1987 in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Nine week response time under black cloth.
2. Six to seven breaks after pinch.
3. Best grown pinched.
4. Top leaves are dark green.
5. Mature leaves are also dark green.
6. Petioles are shiny, waxy and dark brownish-red.
7. Leaves on top are waxy smooth; leaves on bottom are rough because of veins which are shiny green.
8. Stem is green to brownish-red.
9. Bracts are dark red and fade resistant.
10. Cyathia stand strong and are medium tight.
11. Bloom has double rows of the Wonder Star type.
12. Up to twenty (20) bracts on a pinched plant.
13. The largest bloom size measured on a pinched plant has been 11 inches in diameter.
14. Bracts range in size from four (4) cm. to nine (9) cm. wide and nine (9) cm. to twelve (12) cm. long on a pinched plant.
15. In normal blooming the new cultivar shows color by the beginning of November and the bracts are fully developed by the middle of December.
16. Responds well to the growth regulator Cycocel.
17. Plants are long lasting and ship well and are excellent for basket presentation.
18. Ability to grow at temperatures of 65° F. When fully bloomed flower retains its beauty and a life at a temperature of 60° F. and has non-drooping foliage.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on nine week plants. The color readings were determined at 3 p.m. on Feb. 25, 1988 under natural daylight at Sugar Run, Pa. Color references are primarily to the R.H.S. Colour Chart of The Royal Horticultural Society of London.

The plant:

*Form.*—Double compact.

*Growth habit.*—Bracts are flat and shorter than H365 but taller than Wonder Star.

*Rooting.*—Very fast and very uniform.

*Blooming season.*—Nine weeks.

*Blooming habit.*—The blooming is better than other known Annette Hegg varieties.

Foliage:

*Size.*—9 cm. wide and 12 cm. long.

*Quantity.*—Up to eight leaves per stem depending on culture.

*Color.*—New foliage — Upper side, Green Group 137A. Under side, Green Group 137C. Old Foliage — Upper side, Green Group 137B. Under Side, Green Group 137C. Leaf Petiole — Upper side, Greyed-Purple Group 185A. Under side, Greyed-Orange Group 173A.

*Shape.*—Pinched plant is more oak shaped than heart shaped.

*Texture.*—Upper side is smooth; under side is rough because of veins.

*Edge of margin.*—Wavy.

*Veins.*—Midrib to margin. Upper side is light green and under side, Green Group 139D.

Flower: (Cyathia).

*Borne.*—Compact inflorescence.

*Quantity.*—10 to 12; each one has a nectary.

*Color.*—Generally orange and dark red; Green Group 139D.

*Disease resistance.*—Resistant to Botrytis.

Bracts:

*Size.*—4 cm. to 9 cm. wide and 9 cm. to 12 cm. long.

*Veins.*—Midrib to margin.

*Quantity.*—Up to 20 on a fully developed bloom.

*Color.*—Top: Red Group 53 B. Bottom: Red Group 53 C.

*Resistance to fade.*—Excellent for basket.

Reproductive organs: Typical for poinsettia cultivars.

I claim:

1. A new and distinct variety of poinsettia plant as herein shown and described, particularly characterized by its dark red and fade resistant bracts, dark green foliage, double compact form, long lasting keeping qualities and adaptability for basket presentation, and parts therefor.

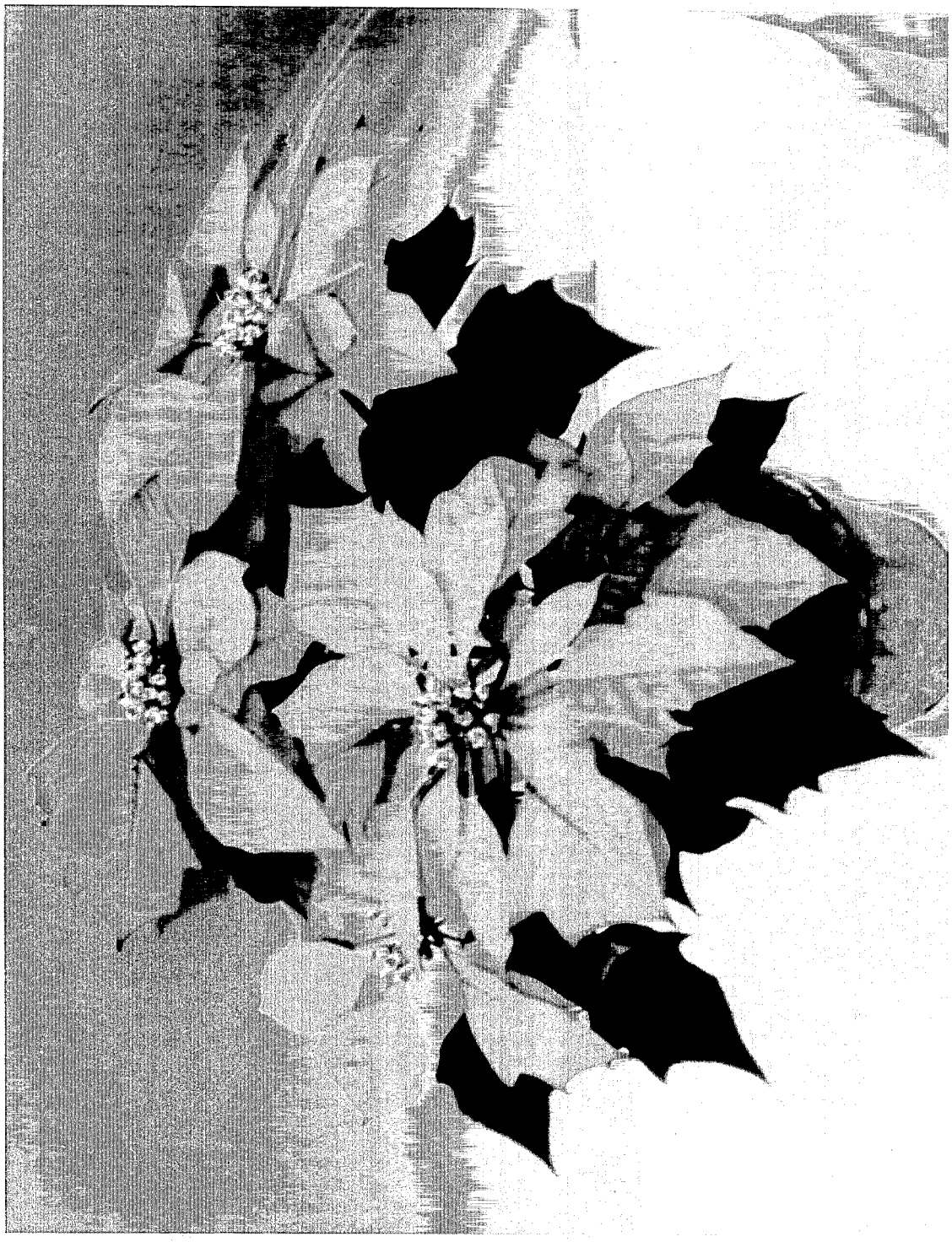

* * * * *